United States Patent
Koinuma

(10) Patent No.: US 8,091,424 B2
(45) Date of Patent: Jan. 10, 2012

(54) DEFECT DETECTION METHOD OF TURBINE GENERATOR END RING

(75) Inventor: Hiroaki Koinuma, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 366 days.

(21) Appl. No.: 12/235,089

(22) Filed: Sep. 22, 2008

(65) Prior Publication Data

US 2009/0095085 A1      Apr. 16, 2009

(30) Foreign Application Priority Data

Oct. 12, 2007   (JP) ................... 2007-267134

(51) Int. Cl.
  *G01N 29/07* (2006.01)
(52) U.S. Cl. ............... 73/598; 73/593; 73/660
(58) Field of Classification Search .......... 73/660, 73/593, 599, 600, 602, 620, 622, 624, 626, 73/644, 598
  See application file for complete search history.

(56) References Cited

U.S. PATENT DOCUMENTS

| | | | | | |
|---|---|---|---|---|---|
| 4,098,129 | A | * | 7/1978 | Deblaere et al. | 73/599 |
| 4,221,312 | A | * | 9/1980 | Wertjes | 224/42.21 |
| 4,408,294 | A | * | 10/1983 | Imam | 702/35 |
| 4,441,369 | A | * | 4/1984 | Lessard et al. | 73/602 |
| 4,457,176 | A | * | 7/1984 | Scholz | 73/624 |
| 5,258,923 | A | * | 11/1993 | Imam et al. | 702/36 |
| 5,335,546 | A | * | 8/1994 | Karbach et al. | 73/622 |
| 6,957,583 | B2 | | 10/2005 | Tooma et al. | 73/625 |
| 7,240,556 | B2 | * | 7/2007 | Georgeson et al. | 73/641 |
| 7,500,396 | B2 | * | 3/2009 | Bentzel | 73/628 |
| 2009/0217763 | A1 | * | 9/2009 | Yamano | 73/622 |

FOREIGN PATENT DOCUMENTS

| | | |
|---|---|---|
| JP | 60-170764 A | 9/1985 |
| JP | 11-287790 | 10/1999 |
| JP | 11287789 A | 10/1999 |
| JP | 2002-310998 A | 10/2002 |
| JP | 2003-194787 A | 7/2003 |
| RU | 523346 | 7/1976 |
| WO | 2007/004303 A1 | 1/2007 |

OTHER PUBLICATIONS

Office Action dated Nov. 25, 2010 (with English translation) from corresponding Chinese Patent Appln No. 200810179972.6.

* cited by examiner

*Primary Examiner* — J M Saint Surin
(74) *Attorney, Agent, or Firm* — Ohlandt, Greeley, Ruggiero & Perle, L.L.P.

(57) ABSTRACT

A defect detection method of a turbine generator end ring includes a first ultrasonic testing step of conducting ultrasonic testing by an angle beam technique to the turbine generator end ring, a second ultrasonic testing step of conducting, when an indication echo is detected by the first ultrasonic testing step, ultrasonic testing by a focusing straight beam technique to a portion of the turbine generator end ring from which an indication echo is detected and an interpretation step of interpreting whether the indication echo is a defect echo or a false echo based on a testing result by the second ultrasonic testing step.

2 Claims, 7 Drawing Sheets

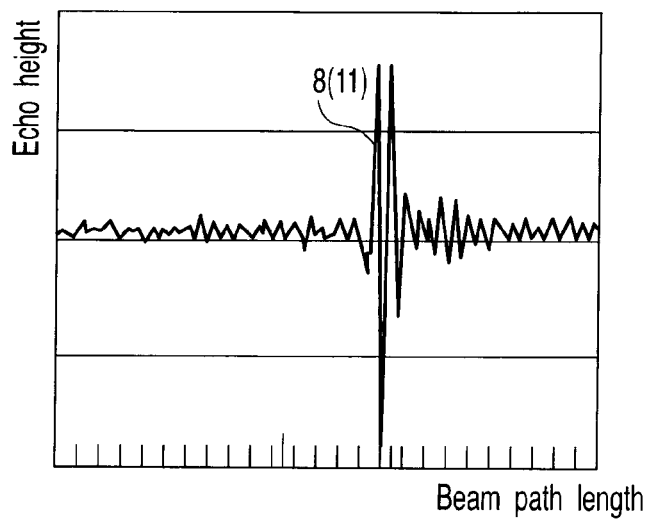
F I G. 10

DEFECT DETECTION METHOD OF TURBINE GENERATOR END RING

CROSS-REFERENCE TO RELATED APPLICATIONS

This application is based upon and claims the benefit of priority from prior Japanese Patent Application No. 2007-267134, filed Oct. 12, 2007, the entire contents of which are incorporated herein by reference.

BACKGROUND OF THE INVENTION

1. Field of the Invention

The present invention relates to a defect detection method of a turbine generator end ring by ultrasonic testing.

2. Description of the Related Art

Ultrasonic testing of a turbine generator end ring is conducted to detect defects such as stress corrosion cracks arising on the surface of the end ring. The ultrasonic testing of the end ring is conducted in an assembled state without disassembling the end ring. The angle beam technique is generally applied to the ultrasonic testing of the end ring. In the ultrasonic testing in which the angle beam technique is applied, an angle beam probe is used to scan the surface of an end ring for defects. The portion of a defect is determined by detecting a defect echo, which is a reflected echo from the defect.

FIG. 11 is a schematic diagram showing a state of ultrasonic wave transmission/reception of an angle beam probe in ultrasonic testing by the angle beam technique. FIG. 12 is a waveform diagram showing a relationship between received input of the angle beam probe and a propagation time of an ultrasonic wave in the ultrasonic testing by the angle beam technique. In FIG. 12, the vertical axis represents the received input of the angle beam probe and the horizontal axis represents the propagation time (beam path length) of the ultrasonic wave. That is, FIG. 12 is displayed in an A-scan. FIG. 12 is shown in a direct current (DC) representation. The same reference numbers are attached to the same components as those in FIG. 11 or 12 and a detailed description thereof is omitted. Similarly, a detailed description is omitted below.

An angle beam probe 2 is installed on the surface of an outer circumferential surface of an end ring 1. In case a defect 4 is present on an inner circumferential surface of the end ring 1, when an ultrasonic wave beam 3 is incident from the angle beam probe 2, the ultrasonic wave beam 3 is reflected by the defect 4. A reflected wave reflected by the defect 4 is received by the angle beam probe 2. The defect 4 is, for example, a stress corrosion crack. At this point, as shown in FIG. 12, a transmission pulse 5 and a defect echo 6 are displayed in the A-scan screen.

In case the defect 4 is not present on the inner circumferential surface of the end ring 1, even though the ultrasonic wave beam 3 is incident from the angle beam probe 2, no reflected wave reflected on the inner circumferential surface is received by the angle beam probe 2. This is because there is no reflector on the inner circumferential surface of the end ring serving as a bottom. Thus, in case the defect 4 is not present, only the transmission pulse 5 is displayed in the A-scan screen and the defect echo 6 is not displayed.

By using the ultrasonic testing by the angle beam technique in this manner, the defect 4 can easily be detected. However, when inspecting defects of an end ring of a turbine generator, attention should be paid to detection of a false echo.

An example in which a false echo is detected in the ultrasonic testing by the angle beam technique will be described with reference to FIGS. 13 to 16. FIG. 13 is a schematic diagram illustrating detection of a false echo 8 by a shaft shrinkage fitting portion 7. FIG. 14 is a waveform diagram in the A-scan DC representation of detection of the false echo 8 by the shaft shrinkage fitting portion 7. FIG. 15 is a schematic diagram illustrating detection of the false echo 8 by a joint portion of a short-circuit ring 9 of the end ring 1. FIG. 16 is a waveform diagram in the A-scan DC presentation of detection of the false echo 8 by the joint portion of the short-circuit ring 9 of the end ring 1.

As shown in FIG. 13, the shaft shrinkage fitting portion 7 is provided on the inner circumferential surface of the end ring 1. The shaft shrinkage fitting portion 7 normally has a substantially rectangular section in contact with the end ring 1. The short-circuit ring 9 is arranged, as shown in FIG. 15, on the inner circumferential surface of the end ring 1 along a circumferential direction. The short-circuit ring 9 is normally arranged in the circumferential direction by being divided into a plurality of portions. Thus, an edge of one of the divided short-circuit ring 9 becomes a short-circuit ring joint portion with another of the divided short-circuit ring 9.

If the ultrasonic testing by the angle beam technique is conducted when an edge of the shaft shrinkage fitting portion 7 or a joint portion of the short-circuit ring 9 is present on the inner circumferential surface of the end ring 1, the following will occur.

The ultrasonic wave beam 3 incident from the angle beam probe 2 is reflected by the edge of the shaft shrinkage fitting portion 7 or the joint portion of the short-circuit ring 9 as a reflector. A reflected wave reflected by the reflector is received by the angle beam probe 2. As shown in FIGS. 14 and 16, the reflected wave becomes the false echo 8. When displayed in the A-scan, it is difficult to distinguish the false echo 8 from the defect echo 6 shown in FIG. 12.

A method described in Jpn. Pat. Appln. KOKAI Publication No. 11-287790 is known as a method of distinguishing defect echoes from false echoes. In the method according to this technology, the ultrasonic testing by the angle beam technique is first conducted by depth scanning. Next, split spectrum processing (SSP) of a testing signal obtained from the ultrasonic testing is performed to determine an indication length. Whether an indication is a defect echo or a false echo is interpreted based on the indication length.

However, the above interpretation method is applied to austenite stainless steel. Austenite stainless steel has larger crystal grains compared with ferrite material. Crystal grains of austenite stainless steel often become still larger at a boundary of welding or the like. This interpretation method is intended to interpret false echoes generated by an ultrasonic wave incident near a boundary of welding of such austenite stainless steel being reflected, refracted, or scattered. In contrast, false echoes generated when defects of a turbine generator end ring are detected do not result from the size of crystal grains of material. As shown in FIGS. 13 to 16, false echoes in a turbine generator end ring result from a structure such as the shaft shrinkage fitting portion 7 or a joint portion of the short-circuit ring 9 present on the inner circumferential surface of the end ring 1. Thus, it is very difficult to distinguish false echoes from defect echoes in a turbine generator end ring by using the interpretation method described in Jpn. Pat. Appln. KOKAI Publication No. 11-287790 or the like.

Thus, a defect of the turbine generator end ring 1 is interpreted in the following way. In case an indication echo is displayed in the ultrasonic testing by the angle beam technique, an internal structure diagram is further referenced. In case a structure such as the shaft shrinkage fitting portion 7 or a joint portion of the short-circuit ring 9 is present at a portion where the indication echo is displayed, the indication echo is presumed to be a false echo. In case such a structure is not present, the indication echo is presumed to be a defect echo. However, this interpretation method may not be able to sufficiently detect defects of a turbine generator end ring particularly in the vicinity of an internal structure.

BRIEF SUMMARY OF THE INVENTION

It is an object of the present invention to provide a defect detection method of a turbine generator end ring capable of identifying defect echo or false echoes detected by ultrasonic testing of the turbine generator end ring.

According to an aspect of the present invention, a defect detection method of a turbine generator end ring comprises a first ultrasonic testing step of conducting ultrasonic testing by an angle beam technique to the turbine generator end ring; a second ultrasonic testing step of conducting, when the indication echo is detected by the first ultrasonic testing step, ultrasonic testing by a focusing straight beam technique to a portion of the turbine generator end ring from which an indication echo is detected; and an interpretation step of interpreting whether the indication echo is a defect echo or a false echo based on a testing result by the second ultrasonic testing step.

BRIEF DESCRIPTION OF THE SEVERAL VIEWS OF THE DRAWING

FIG. 10 is a waveform diagram showing the ultrasonic wave reception in the ultrasonic testing by the SPOD technique according to the second embodiment in the A-scan RF representation;

DETAILED DESCRIPTION OF THE INVENTION

Embodiments of the present invention will be described below with reference drawings.

First Embodiment

Figure 1:
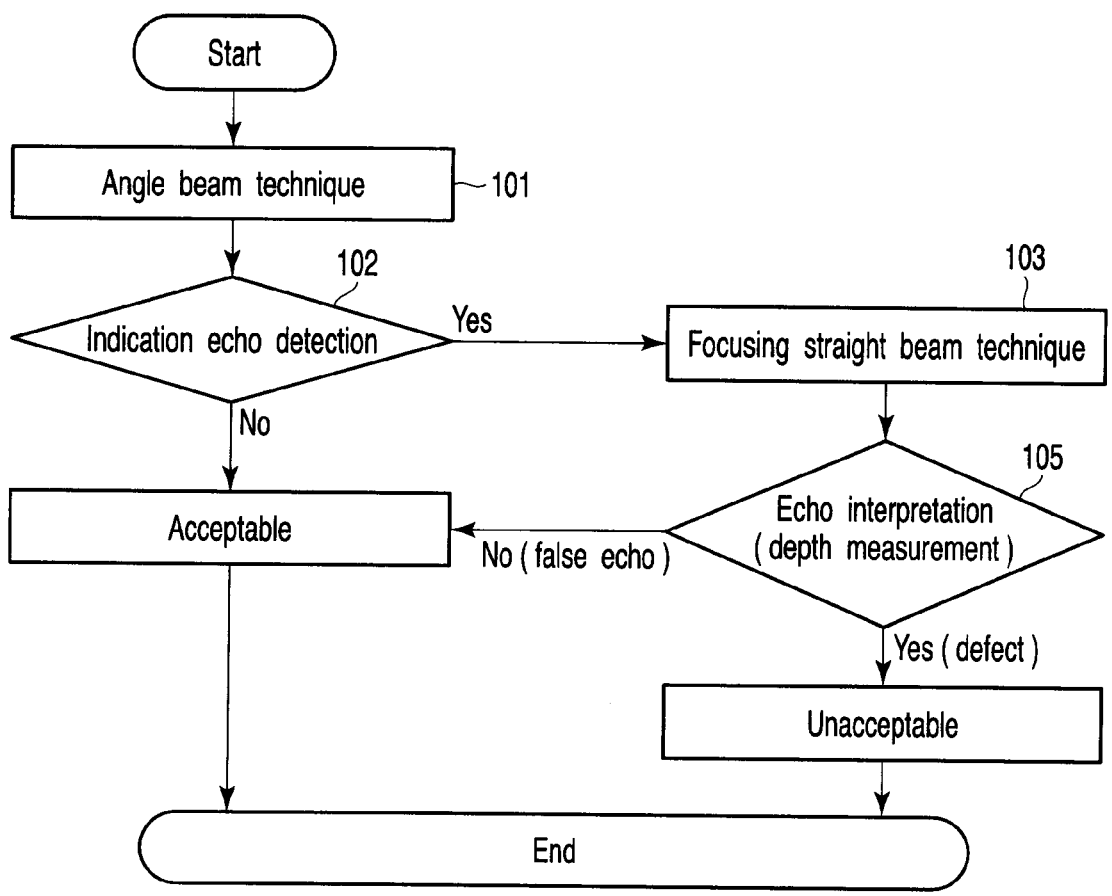
FIG. 1 is a flowchart showing a procedure of a defect detection method of a turbine generator end ring according to a first embodiment of the present invention.

FIG. 1 is a flowchart showing the procedure for the defect detection method of a turbine generator end ring according to the first embodiment of the present invention.

The defect detection method of a turbine generator end ring according to the present embodiment is applied, as shown in FIG. 1, according to the procedure below.

First, an operator conducts ultrasonic testing applying the angle beam technique to a turbine generator end ring (step 101). The operator determines whether or not an indication echo is detected by the ultrasonic testing applying the angle beam technique (step 102). In case the operator determines that no indication echo is detected, the operator judges that the end ring has passed this testing (the turbine generator end ring has no defects) (No in step 102). In case the operator determines that an indication echo is detected (Yes in step 102), the operator conducts the ultrasonic testing applying the focusing straight beam technique to the portion where the indication echo of the turbine generator end ring was detected (step 103). The operator interprets whether or not the indication echo is a defect echo or a false echo from a result of the ultrasonic testing applying the focusing straight beam technique (step 105). If the operator determines that, as a result of interpretation, the indication echo is a defect echo, the operator determines that the turbine generator end ring has a defect. If the operator determines that the turbine generator end ring has a defect, the operator measures a defect depth.

Details of the ultrasonic testing by the focusing straight beam technique (step 103 in FIG. 1) and interpretation of echoes (step 105 in FIG. 1) will be described with reference to FIGS. 2 to 4. The defect detection method described here detects defects on the inner circumferential surface of a turbine generator end ring.

Figure 2:
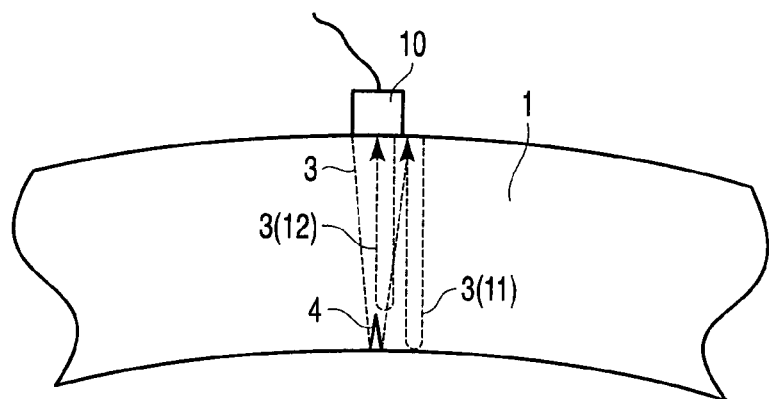
FIG. 2 is a schematic diagram showing a state of ultrasonic wave transmission/reception of a focusing straight beam probe in ultrasonic testing by the focusing straight beam technique according to the first embodiment.

FIG. 2 shows a state of transmission/reception of an ultrasonic wave of a focusing straight beam probe 10. FIG. 3 shows a waveform of an ultrasonic wave 3 received in ultrasonic testing by the focusing straight beam technique in the A-scan DC representation. FIG. 4 enlarges the waveform at the bottom of the turbine generator end ring in FIG. 3 by the A-scan radio frequency (RF) representation.

The ultrasonic testing by the focusing straight beam technique is a method suitable for detection of a dense defect in which a tip branches off into a plurality of portions. According to this method, one divided tip of the dense defect can be caught. Thus, dense defects frequently observed in stress corrosion cracks can effectively be detected.

As shown in FIG. 2, the ultrasonic testing by the focusing straight beam technique is conducted by receiving a reflected wave of the incident ultrasonic wave 3 incident from the focusing straight beam probe 10 by the focusing straight beam probe 10.

The focusing straight beam probe 10 is installed on the surface of the outer circumferential surface of the end ring 1. In case the defect 4 is present on the inner circumferential surface of the end ring 1, when the ultrasonic wave beam 3 is incident from the focusing straight beam probe 10, the focusing straight beam probe 10 receives a reflected wave (a defect tip echo 12) reflected by an edge of the defect 4. The defect 4 is, for example, stress corrosion cracks or fatigue fractures. Then, the focusing straight beam probe 10 receives a reflected wave (a bottom echo 11) reflected by the inner circumferential surface of the end ring 1. Thus, as shown in FIGS. 3 and 4, the transmission pulse 5, the defect tip echo 12, and the bottom echo 11 are displayed in the A-scan screen. The depth of the defect 4 can be determined by examining a beam length difference between the defect tip echo 12 and the bottom echo 11.

In case the defect 4 is not present on the inner circumferential surface of the end ring 1, when the ultrasonic wave beam 3 is incident from the focusing straight beam probe 10, the focusing straight beam probe 10 receives only a reflected wave reflected by the inner circumferential surface of the end ring 1. In this case, only the transmission pulse 5 and the bottom echo 11 are displayed in the A-scan screen and the defect tip echo 12 is not displayed. In case, for example, the shaft shrinkage fitting portion 7 or a joint portion of the short-circuit ring 9 is present on the inner circumferential surface of the end ring 1, a false echo like the defect tip echo 12 is not generated. At this point, only the bottom echo 11 is displayed in the A-scan screen. Accordingly, the operator can determine that the end ring 1 has no defects.

According to the present embodiment, an operation effect described below can be achieved.

Figure 3:
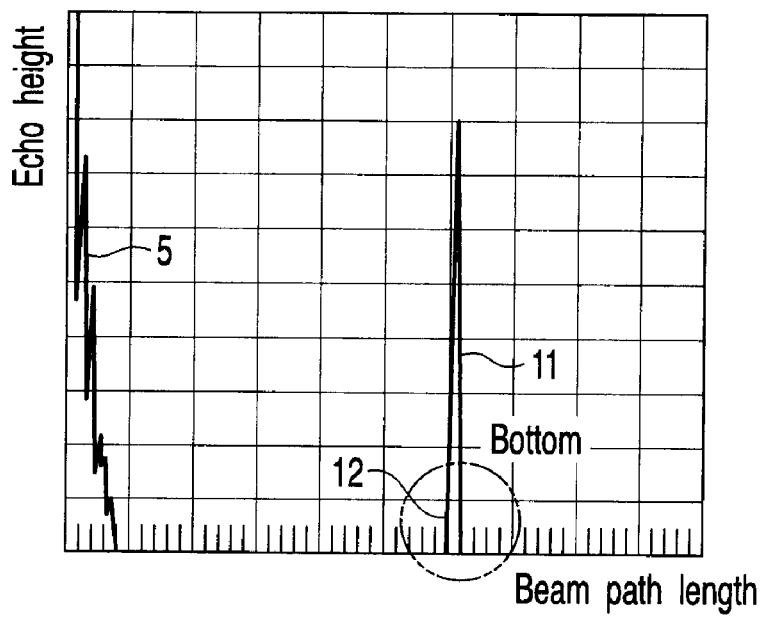
FIG. 3 is a waveform diagram showing ultrasonic wave reception in the ultrasonic testing by the focusing straight beam technique according to the first embodiment in the A-scan DC representation.
Figure 4:
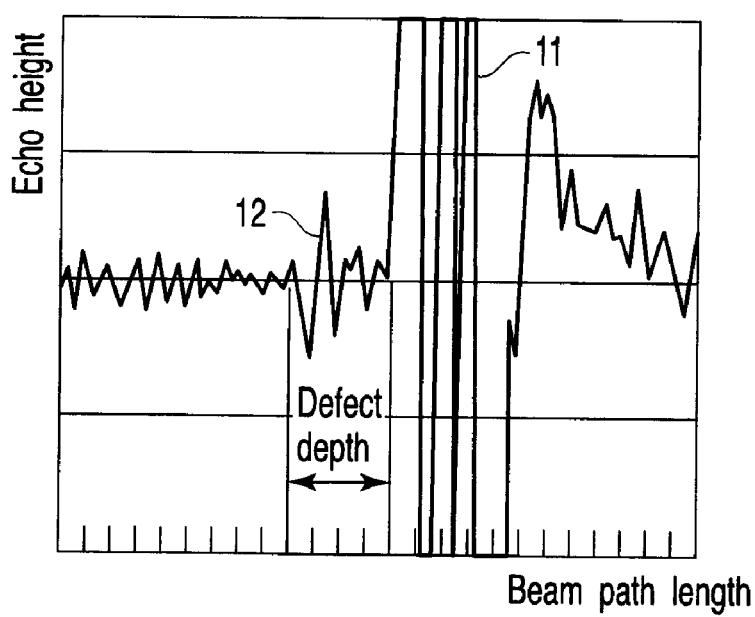
FIG. 4 is a waveform diagram enlarging a waveform at the bottom of the turbine generator end ring in FIG. 3 in the A-scan RF representation.

In ultrasonic testing by the focusing straight beam technique, the defect tip echo 12 obtained when the defect 4 is present is, as shown in FIGS. 3 and 4, smaller than the bottom echo 11. Thus, it is difficult for the ultrasonic testing by the focusing straight beam technique to detect the defect 4 by moving the probe broadly for scanning like the ultrasonic testing by the angle beam technique. Such ultrasonic testing demands proficiency of an operator.

The defect detection method of a turbine generator end ring according to the present embodiment is a combination of the ultrasonic testing by the angle beam technique and that by the focusing straight beam technique. According to the present defect detection method, the ultrasonic testing by the focusing straight beam technique is conducted to a portion from which an indication echo is obtained in the ultrasonic testing by the angle beam technique. The indication echo is determined whether the indication echo results from the defect 4 or is a false echo by the ultrasonic testing applying the focusing straight beam method. According to this method, an operator can easily and reliably detect only the defect 4. The ultrasonic testing by the focusing straight beam technique can catch one divided tip of a dense defect. Thus, the present defect detection method can efficiently detect a defect in case the defect 4 is a dense defect frequently observed in stress corrosion cracks.

The present defect detection method can not only determine presence/absence of a defect by doing the ultrasonic testing by the focusing straight beam technique to a portion from which an indication echo is obtained in the ultrasonic testing by the angle beam technique, but also measure the depth of the defect.

The ultrasonic testing by the angle beam technique has high detection sensitivity. However, a false echo may arise when the ultrasonic testing by the angle beam technique is applied. On the other hand, the ultrasonic testing by the focusing straight beam technique has, low detection sensitivity. However, no false echo arises when the ultrasonic testing by the focusing straight beam technique is applied. Thus, according to the present defect detection method, the ultrasonic testing by the angle beam technique having high detection sensitivity is first applied. Next, the ultrasonic testing by the focusing straight beam technique causing no false echo is further applied to a portion from which an indication echo is received. Accordingly, an operator can reliably detect the defect 4 of the turbine generator end ring 1 with a small amount of time and effort without the need for an internal structure diagram of the end ring.

Therefore, even if a false echo is generated resulting from an internal structure provided on the inner circumferential surface of an end ring like a turbine generator end ring, an operator can distinguish defect echoes from false echoes by using the present defect detection method without the need for an internal structure diagram of the end ring. Therefore, the operator can effectively detect defects of the turbine generator end ring.

Moreover, the present defect detection method can be applied without disassembling a turbine generator rotor. Therefore, tests according to the present defect detection method can be conducted at the work site where the turbine generator is installed. Thus, an operator can shorten a period needed for such tests.

Second Embodiment

Figure 5:
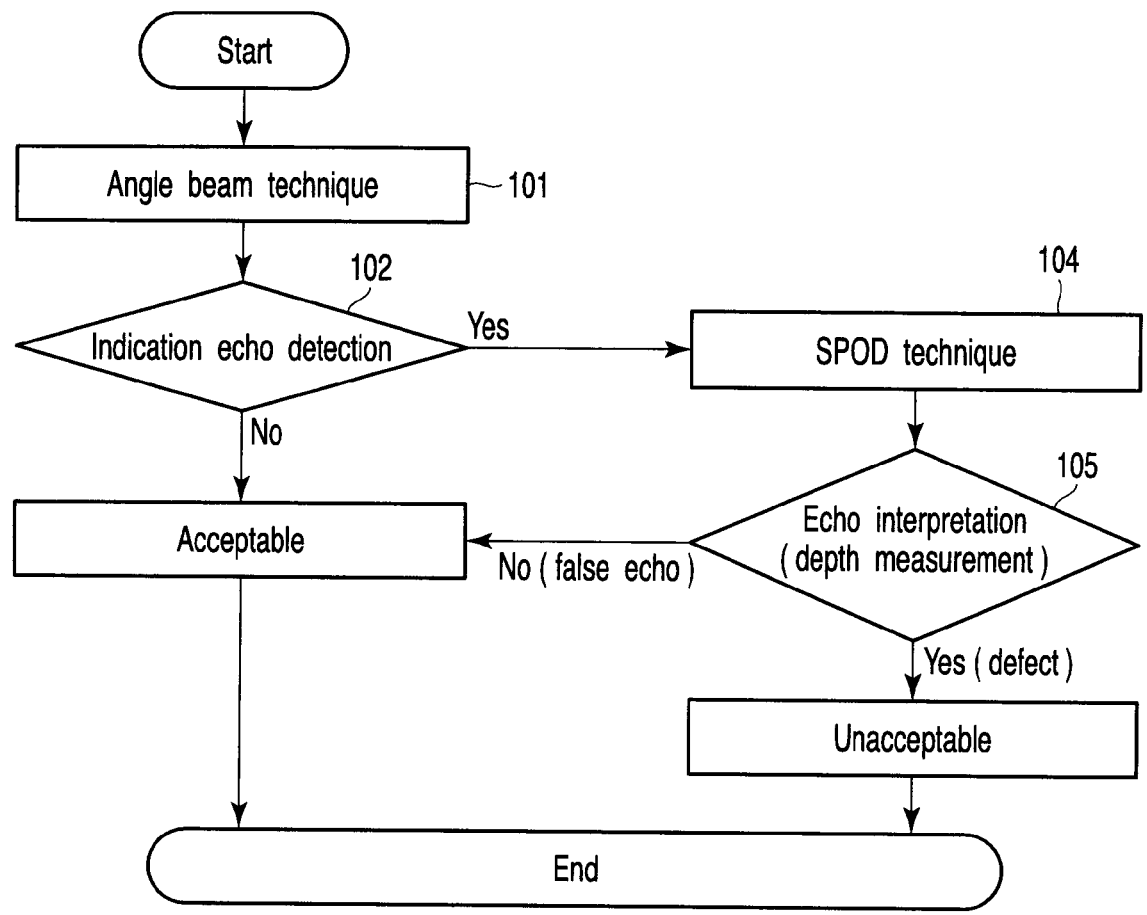
FIG. 5 is a flowchart showing the procedure of the defect detection method of a turbine generator end ring according to a second embodiment of the present embodiment.

FIG. 5 is a flowchart showing the procedure of the defect detection method of a turbine generator end ring according to the second embodiment of the present embodiment.

The defect detection method of a turbine generator end ring according to the present embodiment is obtained by replacing the ultrasonic testing by the focusing straight beam technique (step 103 in FIG. 1) in the defect detection method of a turbine generator end ring according to the first embodiment shown in FIG. 1 with the ultrasonic testing by the short path of diffraction (SPOD) technique (step 104). Otherwise, the defect detection method according to the present embodiment is the same procedure as that of the defect detection method of a turbine generator end ring according to the first embodiment.

The defect detection method of a turbine generator end ring according to the present embodiment is conducted, as shown in FIG. 5, according to the following procedure.

First, an operator conducts the ultrasonic testing applying the angle beam technique to a turbine generator end ring (step 101). The operator determines whether or not an indication echo is detected by the ultrasonic testing applying the angle beam technique (step 102). If the operator determines that no indication echo is detected, the operator judges that the end ring has passed this testing (the turbine generator end ring has no defects) (No in step 102). If the operator determines that an indication echo is detected (Yes in step 102), the operator conducts the ultrasonic testing applying the SPOD technique to the portion where the indication echo of the turbine generator end ring was detected (step 104). The operator interprets whether or not the indication echo is a defect echo or a false echo from a result of the ultrasonic testing applying the SPOD technique (step 105). If the operator determines that, as a result of interpretation, the indication echo is a defect echo, the operator determines that the turbine generator end ring has a defect. If the operator determines that the turbine generator end ring has a defect, the operator measures a defect depth.

Details of the ultrasonic testing by the SPOD technique (step 104 in FIG. 5) and interpretation of echoes (step 105 in FIG. 5) will be described with reference to FIGS. 6 and 7. The defect detection method described here detects defects on the inner circumferential surface of a turbine generator end ring.

Figure 6:
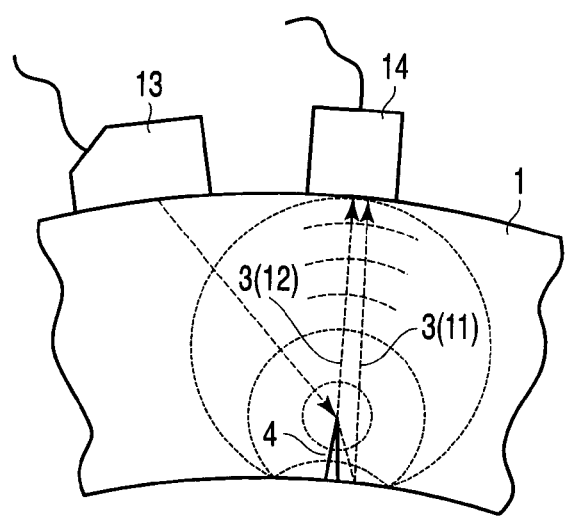
FIG. 6 is a schematic diagram showing a state of ultrasonic wave transmission/reception of probes in the ultrasonic testing by the SPOD technique according to the second embodiment.
Figure 7:
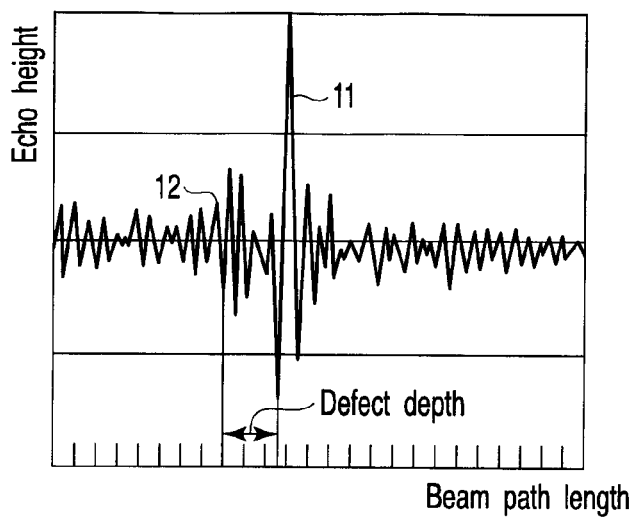
FIG. 7 is a waveform diagram showing ultrasonic wave reception in the ultrasonic testing by the SPOD technique according to the second embodiment in the A-scan RF representation.

FIG. 6 shows a state of ultrasonic wave transmission/reception of probes 13/14. FIG. 7 shows a waveform of the ultrasonic wave 3 received in the ultrasonic testing by the SPOD technique in the A-scan RF representation.

The ultrasonic testing by the SPOD technique is a method suitable for detection of a defect whose tip is closed. According to this testing, defects whose tip is closed (directional defects) frequently observed in fatigue fractures can effectively be detected.

As shown in FIG. 6, the ultrasonic testing by the SPOD technique is conducted by receiving a reflected wave of the incident ultrasonic wave 3 incident from the transmitting angle beam probe 13 by the receiving straight beam probe 14.

The transmitting angle beam probe 13 is installed on the surface of the outer circumferential surface of the end ring 1. The receiving straight beam probe 14 is installed on the surface of the outer circumferential surface of the end ring 1 positioned immediately above the defect 4. In case the defect 4 is present on the inner circumferential surface of the end ring 1, when the ultrasonic wave beam 3 is incident from the transmitting angle beam probe 13, straight beam probe 14 receives a reflected wave (the defect tip echo 12) reflected by an edge of the defect 4. The defect 4 is, for example, a stress corrosion crack or fatigue fracture. Then, the receiving straight beam probe 14 receives a reflected wave (the bottom echo 11) reflected by the inner circumferential surface of the end ring 1. Thus, as shown in FIG. 7, the defect tip echo 12 and the bottom echo 11 are displayed in the A-scan screen. The depth of the defect 4 can be determined by examining a beam length difference between the defect tip echo 12 and the bottom echo 11.

Details of the ultrasonic testing by the SPOD technique (step 104 in FIG. 5) and interpretation of echoes (step 105 in FIG. 5) will be described with reference to FIGS. 8 to 10. The defect detection method described here detects defects on the inner circumferential surface of a turbine generator end ring.

Figure 8:
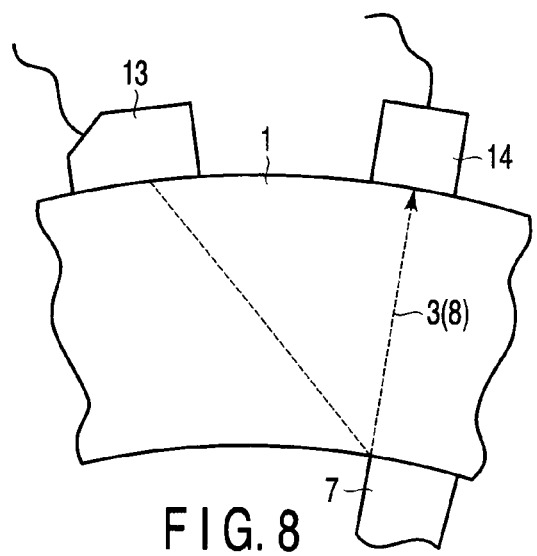
FIG. 8 is a schematic diagram showing a state of ultrasonic wave transmission/reception of the probes in the ultrasonic testing by the SPOD technique according to the second embodiment when a shaft shrinkage fitting portion is present.
Figure 9:
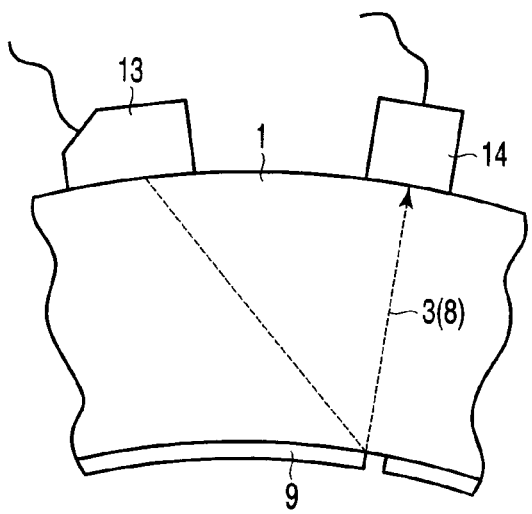
FIG. 9 is a schematic diagram showing a state of ultrasonic wave transmission/reception of the probe in the ultrasonic testing by the SPOD technique according to the second embodiment when a short-circuit ring joint portion is present.
Figure 11:
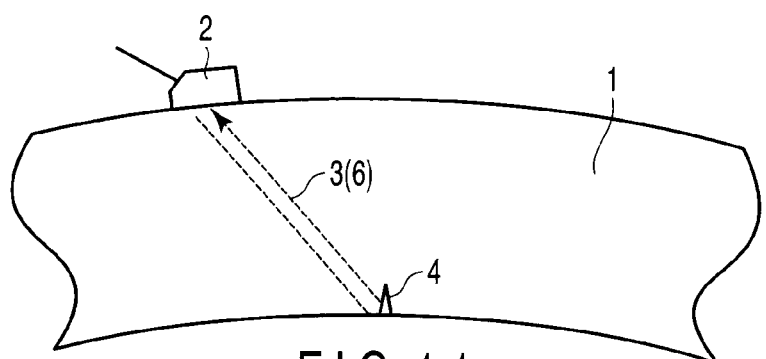
FIG. 11 is a schematic diagram showing a state of ultrasonic wave transmission/reception of an angle beam probe in the ultrasonic testing by the angle beam technique.
Figure 12:
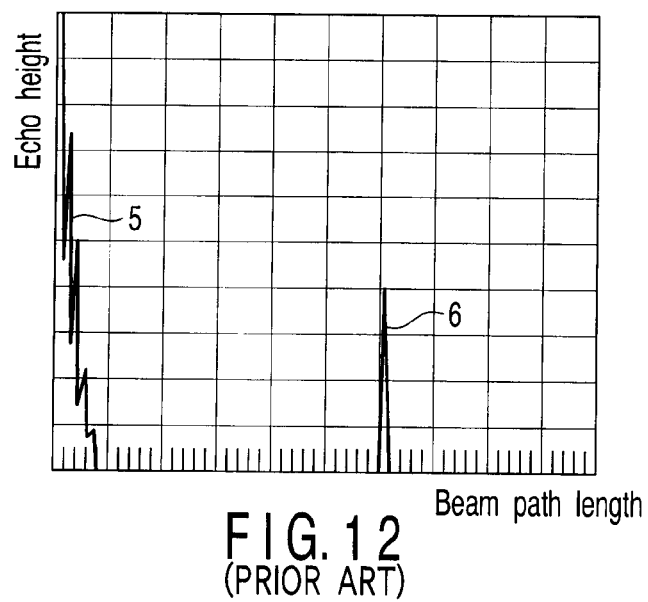
FIG. 12 is a waveform diagram showing the ultrasonic wave reception in the ultrasonic testing by the angle beam technique in the A-scan DC representation.
Figure 13:
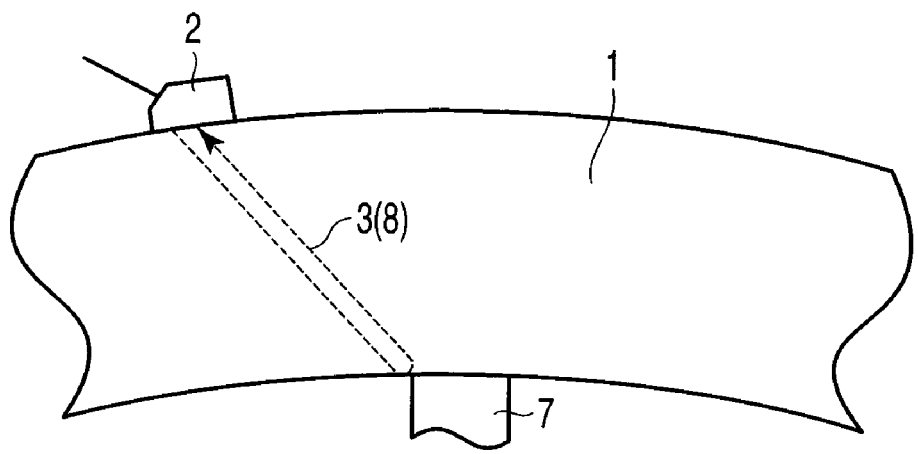
FIG. 13 is a schematic diagram illustrating detection of a false echo by a shaft shrinkage fitting portion in the ultrasonic testing by the angle beam technique.
Figure 14:
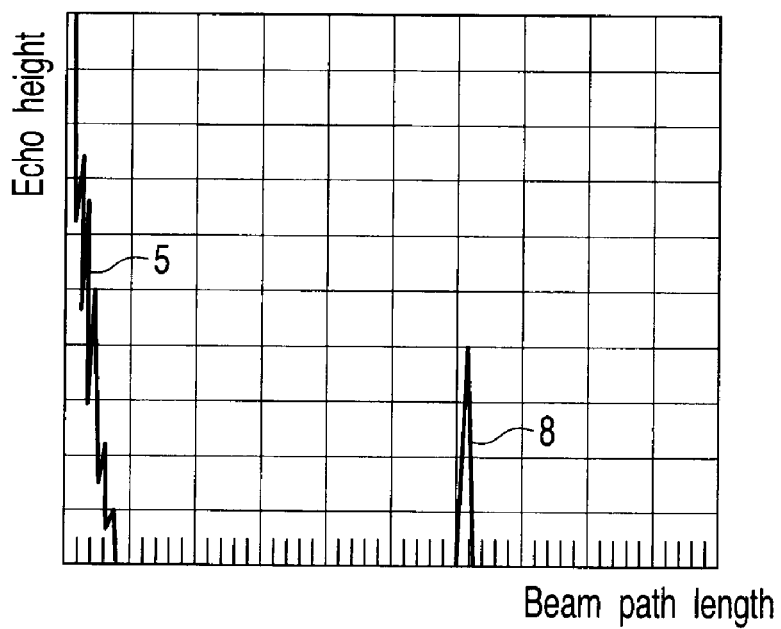
FIG. 14 is a waveform diagram showing detection of the false echo by the shaft shrinkage fitting portion in the ultrasonic testing by the angle beam technique in the A-scan DC representation.
Figure 15:
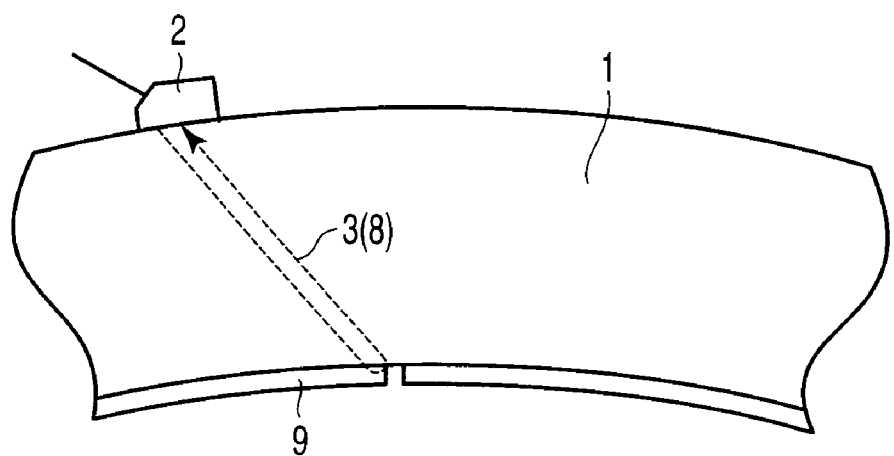
FIG. 15 is a schematic diagram illustrating detection of the false echo by a short-circuit ring joint portion of an end ring in the ultrasonic testing by the angle beam technique.
Figure 16:
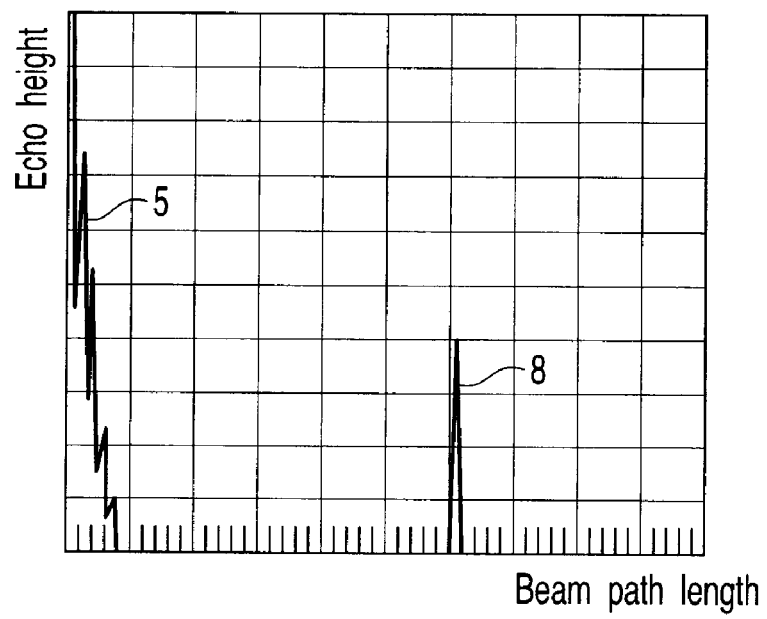
FIG. 16 is a waveform diagram showing detection of the false echo by the short-circuit ring joint portion of the end ring in the ultrasonic testing by the angle beam technique in the A-scan DC representation.

FIG. 8 shows a state of ultrasonic wave transmission/reception of the probes 13/14 when the shaft shrinkage fitting portion 7 is present on the inner circumferential surface of the end ring 1. FIG. 9 shows a state of ultrasonic wave transmission/reception of the probes 13/14 when a joint portion of the short-circuit ring 9 is present on the inner circumferential surface of the end ring 1. FIG. 10 shows a waveform of the ultrasonic wave 3 received in the ultrasonic testing by the SPOD technique in the A-scan RF representation.

If the defect 4 is not present on the inner circumferential surface of the end ring 1, when the ultrasonic wave beam 3 is incident from the transmitting angle beam probe 13, the receiving straight beam probe 14 receives only a reflected wave reflected by the inner circumferential surface of the end ring 1. In this case, as shown in FIG. 10, only the bottom echo 11 is displayed in the A-scan screen and the defect tip echo 12 is not displayed. Even if the shaft shrinkage fitting portion 7 shown in FIG. 8 or a joint portion of the short-circuit ring 9 shown in FIG. 9 is present, a false echo corresponding to the defect tip echo 12 shown in FIG. 7 is not generated. That is, if an indication echo results from the shaft shrinkage fitting portion 7 or a joint portion of the short-circuit ring 9, only the false echo 8 (the bottom echo 11) is displayed in the A-scan screen. Accordingly, an operator can determine that the end ring 1 has no defects.

According to the present embodiment, an operation effect described below can be achieved.

The defect detection method of a turbine generator end ring according to the present embodiment is a combination of the ultrasonic testing by the angle beam technique and that by the SPOD technique. In the ultrasonic testing by the SPOD technique, as well as the ultrasonic testing by the focusing straight beam technique according to the first embodiment, the defect tip echo 12 obtained when the defect 4 is present is, as shown in FIG. 7, smaller than the bottom echo 11. Thus, it is difficult also for the ultrasonic testing by the SPOD technique to detect the defect 4 by moving the probe broadly for scanning. Thus, in the present defect detection method, as well as the first embodiment, the ultrasonic testing by the SPOD technique is conducted to a portion from which an indication echo is received from the ultrasonic testing by the angle beam technique. The indication echo is determined whether the indication echo results from the defect 4 or is a false echo by the ultrasonic testing by the SPOD technique. According to this method, an operator can easily and reliably detect only the defect 4. The ultrasonic testing by the SPOD technique can effectively detect the defect 4 whose tip is closed frequently observed in fatigue fractures. When the ultrasonic testing by the SPOD technique is used, as shown FIGS. 8 to 10, only the bottom echo 8 is obtained when an internal structure is present. Accordingly, the operator can reliably interpret defect echoes and false echoes.

The present defect detection method can not only determine presence/absence of a defect by conducting the ultrasonic testing by the SPOD technique to a portion from which an indication echo is obtained in the ultrasonic testing by the angle beam technique, but also measure the depth of the defect.

The ultrasonic testing by the angle beam technique has high detection sensitivity. However, a false echo may arise when the ultrasonic testing by the angle beam technique is applied. On the other hand, the ultrasonic testing by the SPOD technique has low detection sensitivity. However, no false echo arises when the ultrasonic testing by the SPOD technique is applied. Thus, according to the present defect detection method, the ultrasonic testing by the angle beam technique having high detection sensitivity is first applied. Next, the ultrasonic testing by the SPOD technique causing no false echo is further applied to a portion from which an indication echo is received. Accordingly, an operator can reliably detect the defect 4 of the turbine generator end ring 1 with a small amount of time and effort without the need for an internal structure diagram of the end ring.

Moreover, in the ultrasonic testing by the SPOD technique allows the receiving straight beam probe 14 to freely move fixing the transmitting angle beam probe 13 at the position in which the defect echo or false echo is detected. Accordingly, the operator can make interpretation easier by searching for a peak wave of a waveform to be interpreted. In contrast, in the ultrasonic testing by the time of flight diffraction (TOFD) technique, for example, a transmitting probe and a receiving probe need to be arranged bilaterally symmetrically about an indication to be interpreted. Therefore, the defect detection method using the ultrasonic testing by the TOFD technique cannot obtain the above operation effect of the ultrasonic testing by the SPOD technique because the positions of the transmitting probe and receiving probe are fixed.

Therefore, even if a false echo is generated resulting from an internal structure provided on the inner circumferential surface of an end ring like a turbine generator end ring, an operator can distinguish defect echoes from false echoes by using the present defect detection method without the need for an internal structure diagram of the end ring. Therefore, the operator can effectively detect defects of the turbine generator end ring.

Moreover, the present defect detection method can be conducted without disassembling a turbine generator rotor. Therefore, tests according to the present defect detection method can be conducted at the work site where the turbine generator is installed. Thus, an operator can shorten a period needed for such tests.

Incidentally, in each embodiment, one of the focusing straight beam technique and the SPOD technique is applied, but both the focusing straight beam technique and SPOD technique may be applied. In such a case, a test of one technique or the other may first be conducted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A defect detection method of a turbine generator end ring, comprising:
    conducting a first ultrasonic test by an angle beam technique to the turbine generator end ring;
    conducting, when an indication echo is detected by the first ultrasonic test, a second ultrasonic test by a focusing straight beam technique used for detecting a dense defect or by a short path of diffraction (SPOD) technique used for detecting a defect whose tip is closed to a portion of the turbine generator end ring from which the indication echo is detected; and
    interpreting whether the indication echo is a defect echo or a false echo based on a testing result by the second ultrasonic test.

2. The defect detection method of a turbine generator end ring according to claim 1, further comprising measuring, when an interpretation result by the interpreting step is a defect echo, a defect depth of the defect echo.

* * * * *